(12) United States Patent
Yeutter (10) Patent No.: US 10,697,591 B1
(45) Date of Patent: Jun. 30, 2020

(54) LIGHT BULB WITH CONTROLLED COLOR AND FLICKER

(71) Applicant: Gregory Yeutter, Philadelphia, PA (US)

(72) Inventor: Gregory Yeutter, Philadelphia, PA (US)

( * ) Notice: Subject to any disclaimer, the term of this patent is extended or adjusted under 35 U.S.C. 154(b) by 0 days.

(21) Appl. No.: 16/556,248

(22) Filed: Aug. 30, 2019

(51) Int. Cl.
| | |
|---|---|
| *F21K 9/23* | (2016.01) |
| *H05B 45/00* | (2020.01) |
| *F21K 9/232* | (2016.01) |
| *F21K 9/237* | (2016.01) |
| *F21V 23/02* | (2006.01) |
| *H05B 45/37* | (2020.01) |
| *F21Y 115/10* | (2016.01) |

(52) U.S. Cl.
CPC .............. *F21K 9/232* (2016.08); *F21K 9/237* (2016.08); *F21V 23/023* (2013.01); *H05B 45/37* (2020.01); *F21Y 2115/10* (2016.08)

(58) Field of Classification Search
CPC .......... F21K 9/232; F21K 9/237; F21V 23/02; F21V 23/023; F21Y 2115/10; H05B 37/02; H05B 33/08; H05B 33/0815; H05B 33/0842
See application file for complete search history.

(56) References Cited

U.S. PATENT DOCUMENTS

2016/0238230 A1* 8/2016 Trottier .................. F21V 29/89

\* cited by examiner

*Primary Examiner* — Jimmy T Vu
(74) *Attorney, Agent, or Firm* — Keeley DeAngelo LLP; W Scott Keeley (57) ABSTRACT

A low-luminance LED lamp that produces light designed for evening reading, relaxation and sleep. Low melanopic input balanced with high color rendering and a warm Correlated Color Temperature (CCT) produces a light with reduced circadian/melanopic input. An engineered LED phosphor produces a spectrum with relatively low blue and green content. This is balanced with a high CRI and the preference for warm (low-CCT) lighting in the evening.

10 Claims, 10 Drawing Sheets

LIGHT BULB WITH CONTROLLED COLOR AND FLICKER

TECHNICAL FIELD

The present disclosure relates to optical arrangements integrated in the light source, e.g. for improving the color rendering index or the light extraction; Elements for modifying spectral properties, polarization or intensity of the light emitted, e.g. filters for producing colored light, e.g. monochromatic; for reducing intensity of light.

BACKGROUND

Over the last two decades, scientific studies have revealed the negative impacts of certain types of artificial light on health. New lamps using light-emitting diodes (LEDs) address these findings, adjusting color temperature and flicker to produce a light that reduces negative health impacts.

Human circadian rhythms are known to be disturbed by stimuli from modern technologies. Electronic-device screens expose humans to relatively intense sources of blue and green light at all hours. Before electric light, humans were exposed to only natural sources of light, namely sunlight, moonlight and firelight, but artificial light has reduced the hours spent in sunlight, further disrupting circadian rhythms.

Current lighting products purport to reduce sleep-disturbing blue light but may still produce unhealthy levels of flicker.

Lumens (lm) measure the perceived power of a light source weighted to human vision. This metric is commonly used to define the intensity of a light bulb. A 60-watt incandescent source produces about 650-800 lumens (lm); a 40-watt source produces approximately 400-450 lm.

Luminous flux, measured in lumens (lm), defines the intensity of light produced by a source, while illuminance, measured in lux, is the intensity of light received at the eyes. Lux (lx) is the SI measurement unit of illuminance, measuring luminous flux per area (lumens per square meter) on a surface.

While light levels are commonly specified and measured on the horizontal plane, modern electronic displays are typically oriented as vertical surfaces.

When we stand or sit upright, our eyes perceive light on the vertical plane, and this is how circadian light levels are measured.

Blue-green light stimulates circadian rhythm. The protein melanopsin is activated in the presence of blue and green light.

Equivalent melanopic lux (EML) is a measure of illuminance weighted to the blue-green sensitivity of melanopsin. EML is used to quantify circadian light and is measured on a vertical plane. Illuminance is the total luminous flux per area incident on a surface.

Melanopic lumens are a measure of luminous flux weighted to melanopsin sensitivity. Melanopic lumens can be used to quantify the circadian output of a light source.

Correlated Color Temperature (CCT, or Color Temperature) of a light source is its temperature, expressed in degrees Kelvin (K). A low-CCT LED tends to have a relatively lower luminous efficacy (efficiency) than a high-CCT LED. An evening reading light source should have a nominal CCT between 1800 Kelvin and 2400 Kelvin, to approximate traditional light sources during and post sundown.

"Color rendering" describes a light source's accuracy in rendering reference color samples. The Color-Rendering Index (CRI Ra) is a quantitative measure of a light source's capacity to reveal colors faithfully in comparison with an ideal light source. Sunlight, incandescent, halogen, and some specialized LED sources have CRIs in the high 90s. Modern fluorescent lighting has values in the 80s or 90s. LED lighting typically has a CRI around 80.

TM-30 is a lighting-fidelity metric and and more-descriptive alternative to CRI Ra. Rf is the color rendering fidelity index value for TM-30, which ranges from 0-100. By comparing the 99 TM-30 reference color samples to the rendering of the light source, Rf is computed. A score of 100 is considered to have perfect rendering for all samples.

Rg is another TM-30 metric. An Rg score of 100 means that the light source is, on average, neutrally saturated. Rg from 90-110 is considered very good for general lighting.

Levels of red are expressed in R9, a metric that is not included in calculating CRI Ra. Studies have shown that humans prefer light with high amounts of red. A desirable R9 is 50 or above. Incandescent, halogen, and daylight have R9s of 70 or above. A typical LED source has an R9 close to zero, or even negative.

"Flicker" is rapid, repeated changes in light intensity over time. It is usually invisible and is part of the normal operation of a light source. Magnetic fluorescent ballasts were subject to flicker criticism, but electronic ballasts introduced in the 90s, as well as compact fluorescent lamps, pulse at high speeds (10s of kHz) and have largely solved the flicker problem.

Cheaply-produced LED lights can flicker.

Flicker may be detectable in the presence of moving objects or in the peripheral vision and is known to contribute to headaches, eyestrain and reduced concentration. It is demonstrated in numerous scientific experiments that under flickering light, saccades, or eye movements between two points, do not travel the same distance that they would under steady light. The eyes will overshoot or undershoot the target.

IEEE 1789-2015 is a standard that defines two important flicker metrics: the modulation percentage, which is the interval between the minimum and maximum height of an oscillation; and flicker frequency, which is the frequency of the oscillation in Hz. Because of potential negative consequences of flicker, good lighting schemes are designed to reduce or eliminate it.

Bedtime lighting is designed to minimize circadian input while providing sufficient light for reading. A commonly-recommended indoor task-light level is 500 lx on the horizontal plane. Most home task lighting is between 300 and 700 lx, which has been determined to be uncomfortably bright for the evening. An evening-reading lighting level of 100-200 lx in the horizontal plane is considered ideal for most people.

An evening-reading light source should produce no more than 200 melanopic lumens. This is much lower than a typical 650-800 lumen "soft white" incandescent, halogen, or LED light source, which produces between 330 and 450 melanopic lumens.

A light source ranging from 300 to 450 lumens will produce 100-200 lx in the horizontal plane at 2-4 feet. This is the case for unshaded lamps, in lamps with white and beige shades, and in lamps with white frosted and gray translucent glass globes.

Intrinsically Photosensitive Retinal Ganglion Cells (ipRGCs) are photoreceptors, distinct from rods and cones, which are sensitive to blue and green light. ipRGCs are not used for vision, but they provide an input the circadian rhythm via the retinohypothalamic tract.

LEDs, or light-emitting diodes, are semiconductor devices that emit light when powered.

"A 19" represents a standard light bulb shape, with "19" representing bulb's widest diameter (19/8 inches). A common base for an A19 lamp is the E26 screw (E for Edison screw, 26 mm) in North America. It may be an E27 screw (27 mm), B22 bayonet (Bayonet, 22 mm), or another shape.

"B10" refers to a pointed bulb shape, often referred to as "candelabra," with a diameter of 10/8 inches. B10 lamps typically have an E12 or E26 base.

The directional emission characteristics of LED lamps can cause emitted shadows. Light from an LED lamp directed at a surface may have shadows cast within the diffused light depending on the arrangement of the LEDs in the lamp.

SUMMARY

The present embodiment is a light bulb, also referred to as an LED lamp, having an array of LED packages arranged inside a substantially opaque glass globe with power electronics that produce light designed for viewing printed images and text with relatively low luminance. Glass globes used in lighting range from clear to semi-opaque to opaque.

The embodiment is produced with a glass globe that ranges from semi-opaque to opaque, otherwise referred to as substantially opaque. The light is specifically designed to support evening reading while encouraging relaxation and sleep. The light emitted by the embodiment provides low melanopic input balanced with high color rendering and a warm Correlated Color Temperature (CCT).

To reduce circadian/melanopic input, the LED lamp has an engineered phosphor covering a ~450 nm blue LED that produces a spectrum with relatively low blue and green content. This is balanced with a high CRI and the preference for warm (low-CCT) lighting in the evening.

In one embodiment, an A19 lamp has a specified luminous flux of between 350 lumens to 450 lumens. This is achieved with a 6-watt power conversion circuit attached to eight ~70-volt LEDs. The blue LED dies have a peak wavelength of about 450 nm.

The resulting light is between 100 and 200 lx at 2-4 feet, having a CCT of ~2200 Kelvin, a minimum CRI Ra of 93; a minimum R9 of 50; a minimum Rf of 85; an Rg between 97 and 103; blue light between 440-490 nm, approximately 4%; green light 490-570 nanometers (nm), approximately 17%; and a melanopic ratio between 0.3 and 0.4, preferably 0.39.

LED packages are arranged in a vertical spiral pattern, which has the dual purpose of maximizing the vertical-beam angle of the LED lamp and minimizing shadows. To reduce or eliminate shadows, an array of LED packages is housed in a glass container, the array configured with upper electrical contacts rotated counter-clockwise with respect to lower electrical contacts according to the following equation:

$$R = \frac{360}{n}$$

Where R=the degree of counterclockwise rotation of the upper contacts with respect to the lower electrical contacts, 360=degrees, and n is the number of LED packages. One skilled in the art understands that the 'n' may be replaced by 'n−x' or 'n+x' to produce a similar structure with greater or lesser twist. An array of this nature reduces shadows commonly cast by LED packages when used as lighting. In this LED arrangement, light is directed upward and out to all sides; the lamp is usable in the upright, sideways, or inverted position, ideal for use in a table lamp.

Each LED "filament" package contains 24 blue LED dies in series, arranged in a transparent substrate. The LED package measures approximately 32 mm in length, not including metal electrodes on each end. Each LED die operates at about 2.9 volts each, for a total of about 70 volts (in series). The dies and substrate are coated with a phosphor that produces light of approximately 2200 Kelvin, with a melanopic ratio between 0.30 and 0.40. The LED packages are housed in an exterior diffuser (elsewhere referred to as a glass globe). The light output is between 250 and 450 lumens and between 75 and 180 melanopic lumens.

Reducing melanopic blue and green light produces a light with a low melanopic ratio that encourages relaxation and sleep. However reducing this light by too much reduces the light's efficacy for reading. To balance these factors the embodiment's light has a melanopic ratio between 0.3 and 0.4.

To exceed current recommendations (i.e. IEEE 1789-2015) and prevent negative health consequences associated with flicker, the light source should provide, at frequencies from 100 Hz to 999 Hz, a flicker modulation of less than 10.0%. From 1 kHz to 9.99 kHz, modulation is less than 30.0%, even at the lowest dimming level. 100% modulation is permitted only at 10 kHz or greater. The present embodiment uses a full-wave bridge rectifier with a high level of smoothing capacitance on the DC output of the LED driver. This is designed to provide a flicker modulation of less than 10.0%.

A linear LED driver regulates power to the LEDs. An iteration of the embodiment contains two sets of ~70V filament packages in parallel; the A19-bulb iteration has 2 sets of 4 filaments in parallel, and the B10-bulb iteration has 2 sets of 2 filaments in parallel.

The operating frequency of the LED driver is 120 Hz in North America. For other countries, a similar design operates at about 100 Hz.

In North American models, an electrolytic capacitor rated at at least 160 V is employed. In a 6-watt, 8-filament, A19 iteration of the embodiment, the smoothing capacitor is rated at 15-20 uF.

In a 4-watt, 4-filament, B10 bulb, the smoothing capacitor is rated between 10-12 uF.

DESCRIPTION

Figure 1:
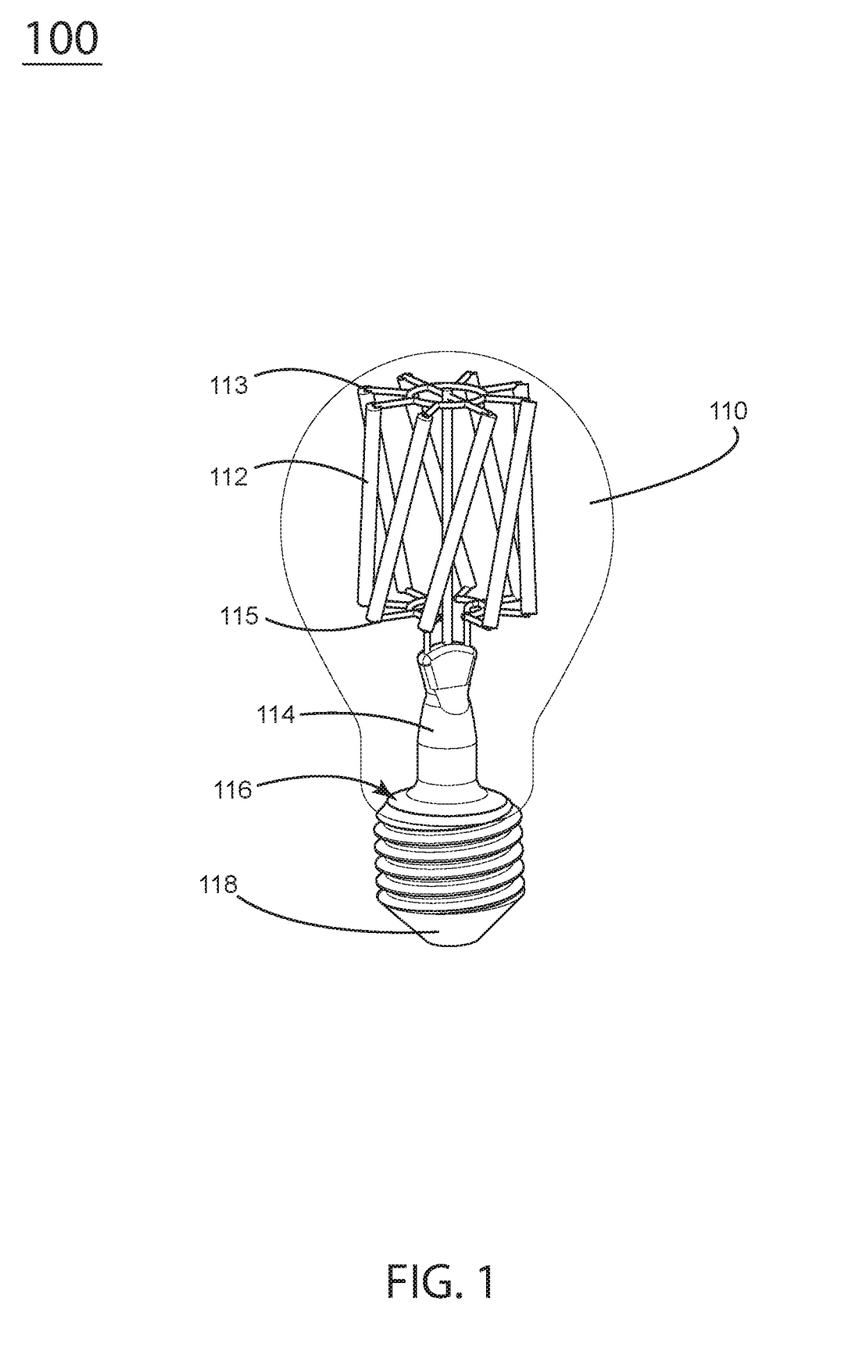
FIG. 1 is a perspective view of a lamp with light-emitting diodes.
Figure 2:
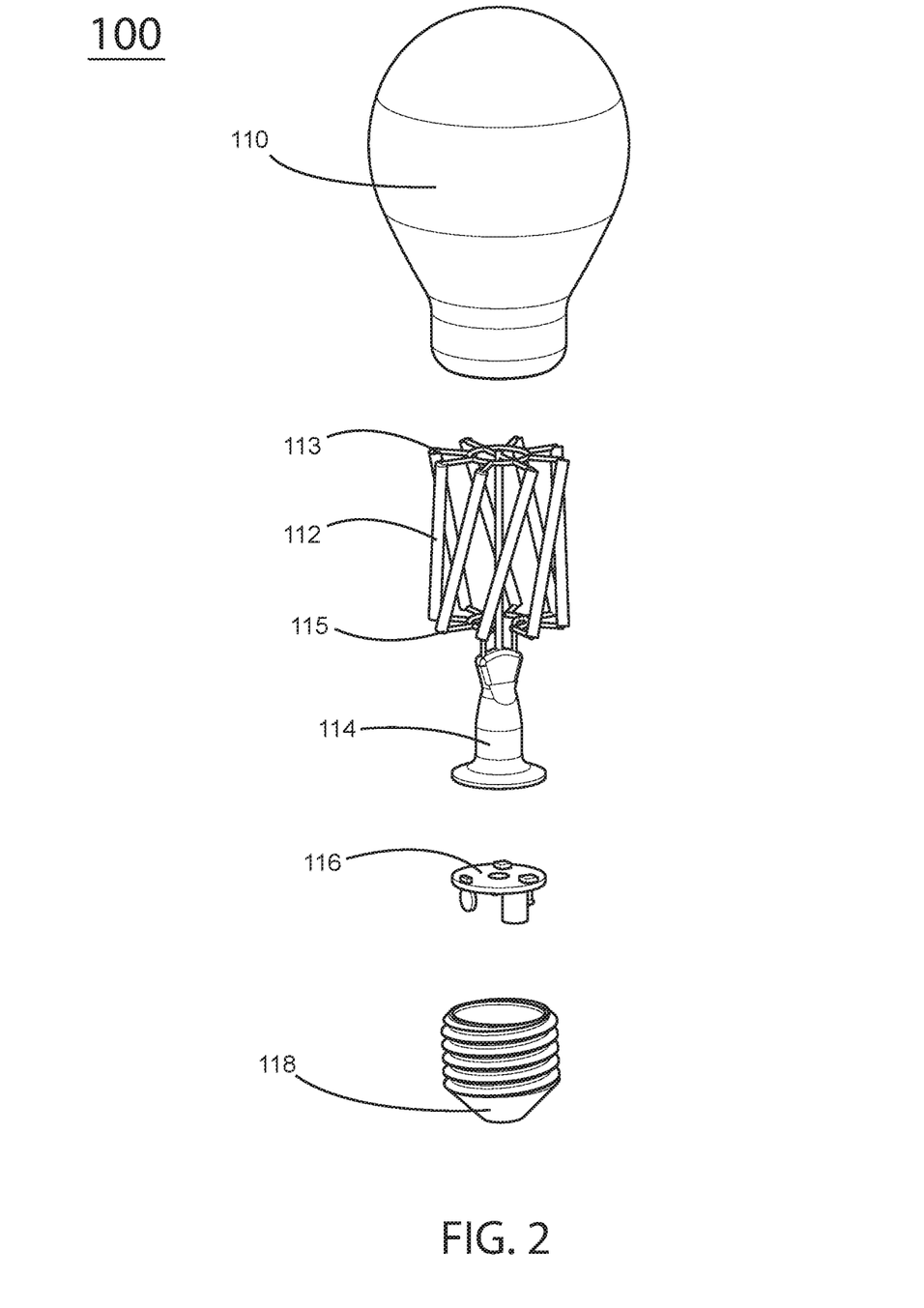
FIG. 2 is an exploded view of the embodiment of FIG. 1.

In FIGS. 1 and 2, an example embodiment 100 shows a glass globe 110 containing an array of light-emitting diodes (LEDs) 112 with upper electrical contacts 113 and lower electrical contacts 115. The LEDs are configured with the upper electrical contacts 113 rotated counter-clockwise with respect to the lower electrical contacts 115 according to the equation $$R = \frac{360}{n}$$

where R=the degree of counterclockwise rotation of the upper contacts 113 with respect to the lower electrical contacts 115, and n is the number of LED packages. One skilled in the art understands that the n may be replaced by n−x or n+x to produce a similar structure with greater or lesser twist. This relative twist in the array of LEDs produces a light with substantially low shadow such that it is not perceivable by the naked eye when the light is cast on a wall or lampshade.

The array of LEDs 112 is mounted on a stem 114 which is electronically coupled to a circuit board 116. The glass globe 110 and stem 114 are engaged with a base 118. The example embodiment is shown with an E26 base. One skilled in the art understands that various bases and variously sized bulbs may be created using variations of these design specifications.

Figure 3:
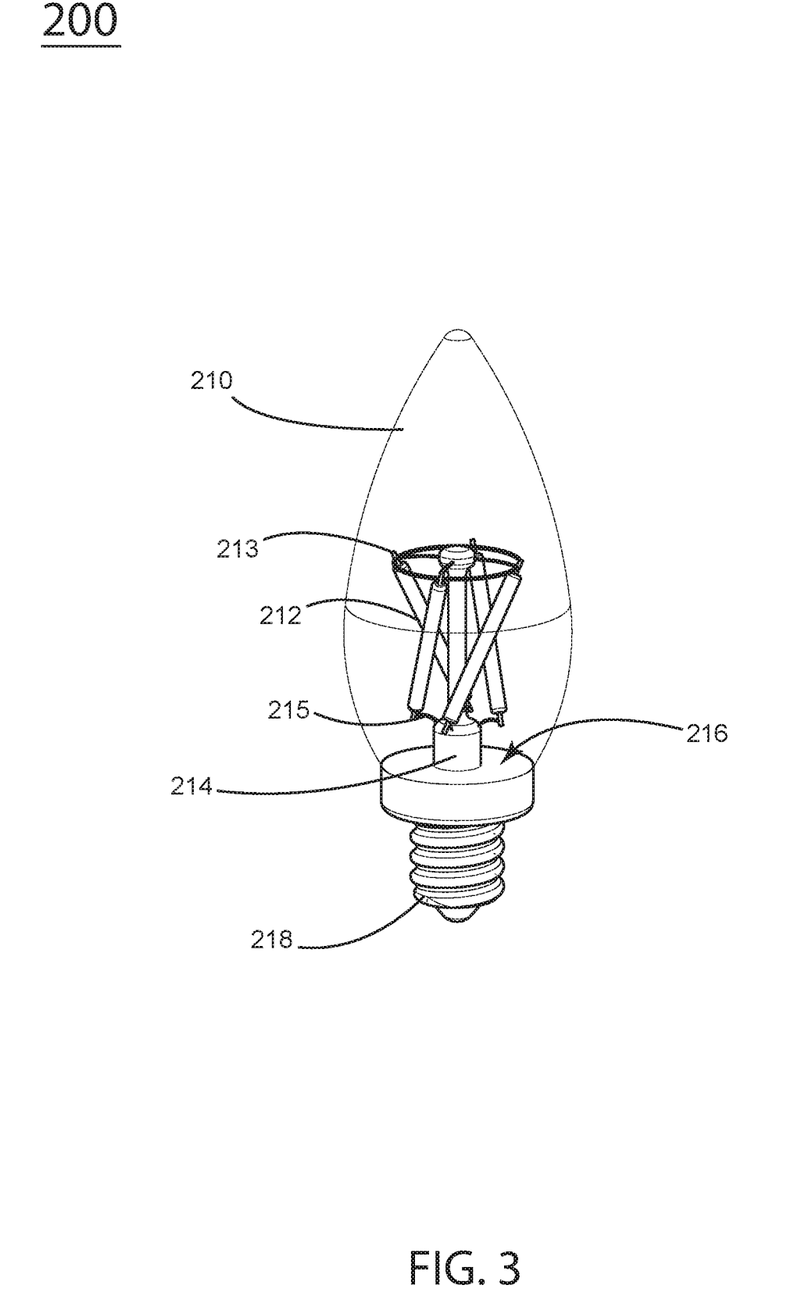
FIG. 3 is a front, perspective view of an iteration of the embodiment.

FIG. 3 shows an iteration of the invention with an E12 base 218. The example iteration 200 comprises a glass globe 210 that contains an array of light-emitting diodes (LEDs) 212 with upper electrical contacts 213 and lower electrical contacts 215. The LEDs are configured with the upper electrical contacts 213 rotated counter clockwise with respect to the lower electrical contacts 215 according to the aforementioned equation. The array of LEDs 212 is contained in a glass globe 210 and mounted on a stem 214 which is electronically coupled to a circuit board 216 located in the base 218 similar to that of FIGS. 1 and 2.

Figure 4:
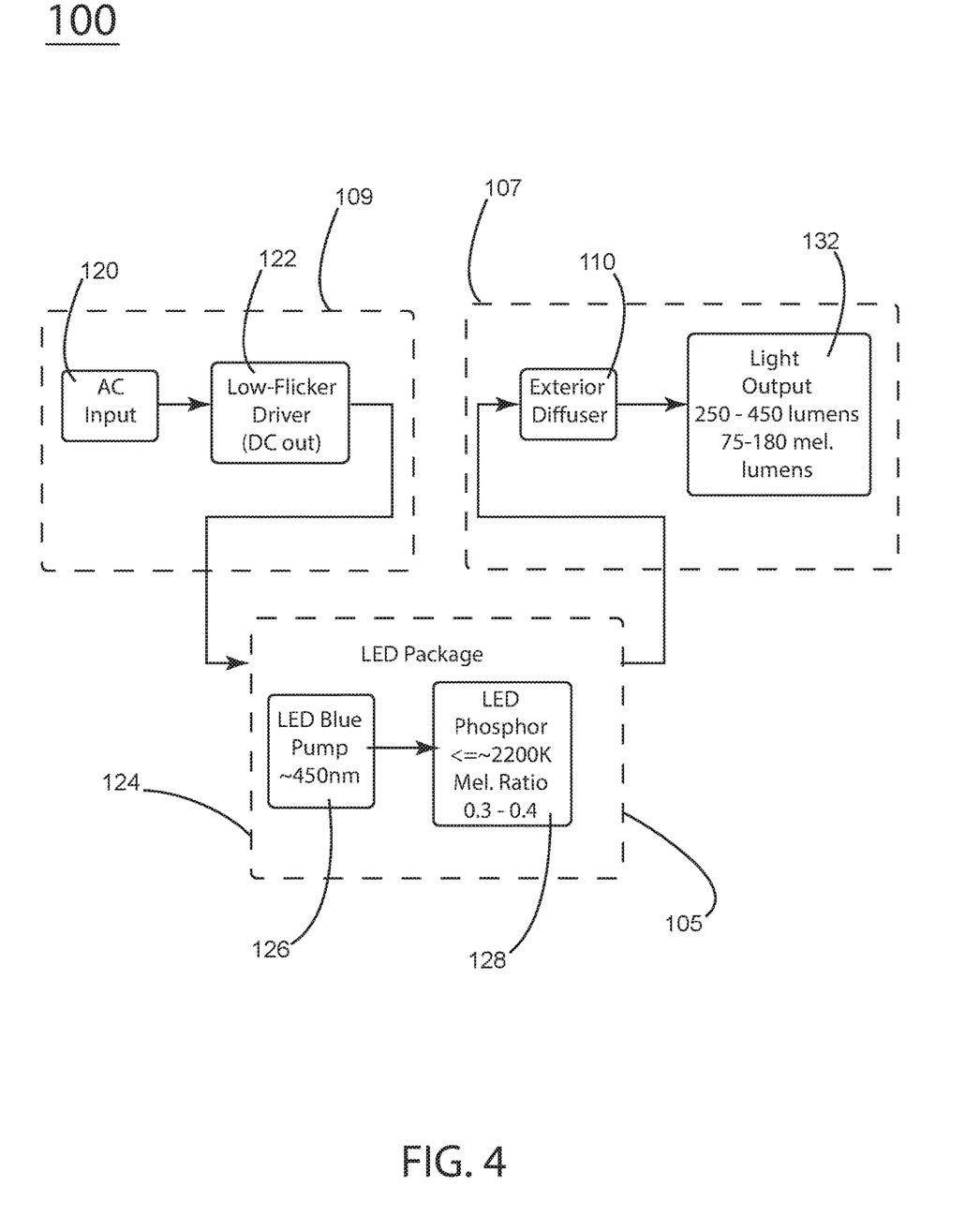
FIG. 4 is a diagram of an example electronic schematic of the embodiment.

FIG. 4 is an electrical schematic of the embodiment. In general, alternating current (AC) 109 is converted to direct current (DC) 105 and is output as light 107. An alternating current (AC) input 120 powers a low-flicker driver 122. One skilled in the art understands a driver, or power supply, may have an AC input with a direct current (DC) output. The low-flicker driver 122 is electrically coupled with an LED array 124 consisting of one or more LED packages. In other words, the low flicker driver changes electrical characteristics of the AC power to provide a conditioned DC current to the LED array. The LED array contains one or more LED packages, each containing at least one LED blue light-emitting diode 126. The blue LED has a peak wavelength of ~450 nm and is coated with a phosphor 128. When illuminated, the phosphor 128 produces light that is approximately 2200 Kelvin, with a melanopic ratio between 0.30 and 0.40. The LED packages are housed in an exterior diffuser (elsewhere referred to as a glass globe) 110. The light output 132 is between 250 and 450 lumens and between 75 and 180 melanopic lumens.

Figure 5:
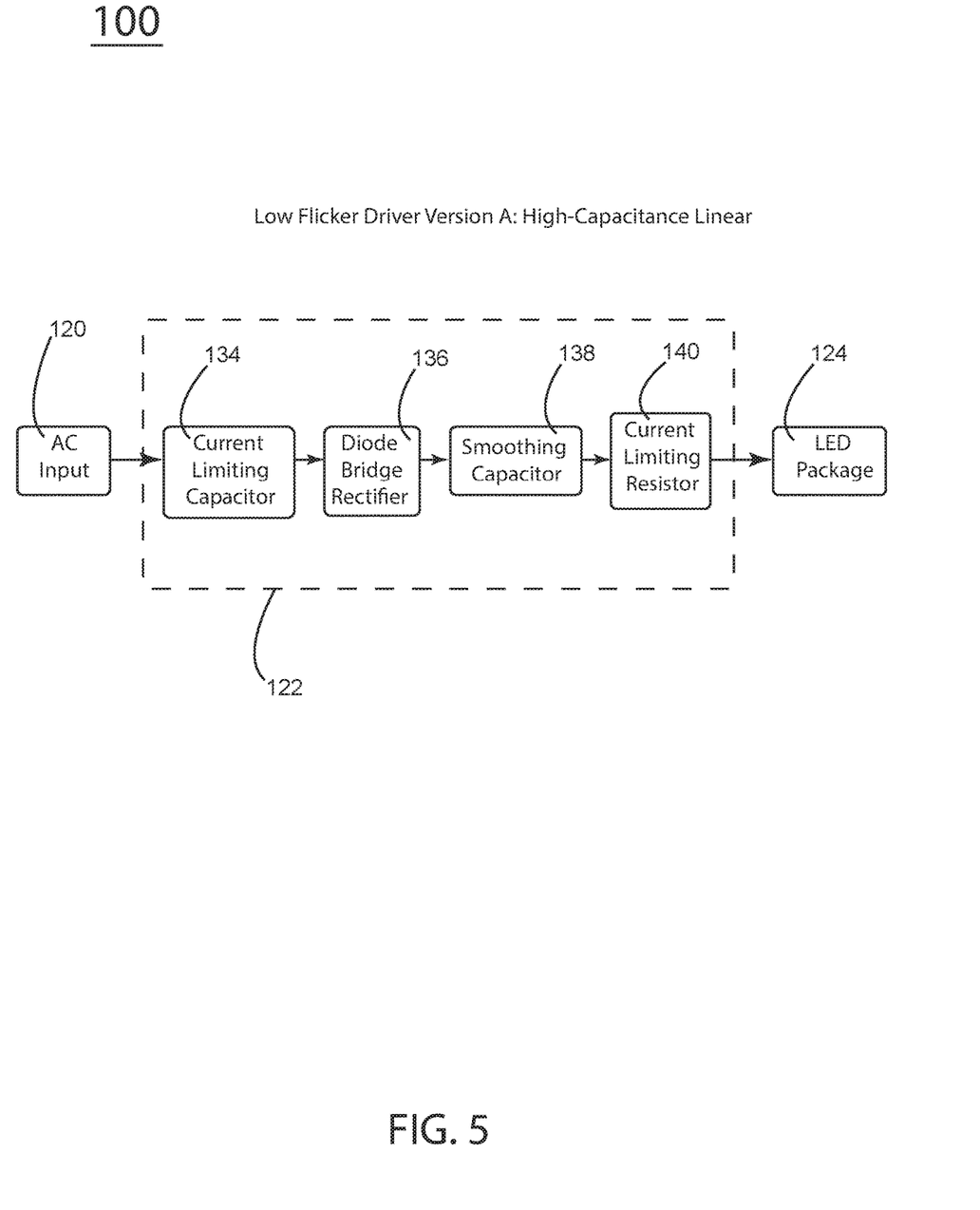
FIG. 5 is a diagram of an example electronic schematic of a low-flicker driver of the embodiment.

FIG. 5 is a diagram depicting a low-flicker driver 122 of the present embodiment, as is briefly described in FIG. 4. One skilled in the art may recognize this LED driver as a linear power supply with high-output capacitance. An AC input 120 powers the low-flicker driver 122. The low-flicker driver 122 is comprised of a current limiting capacitor 134, a diode bridge (referred to as a bridge rectifier) 136, a smoothing capacitor 138, and a current-limiting resistor 140 that in turn powers an LED package 124 (FIG. 4). One skilled in the art understands that an LED array may contain multiple copies of the LED package such as the array shown in FIGS. 1, 2 and 3.

Figure 6:
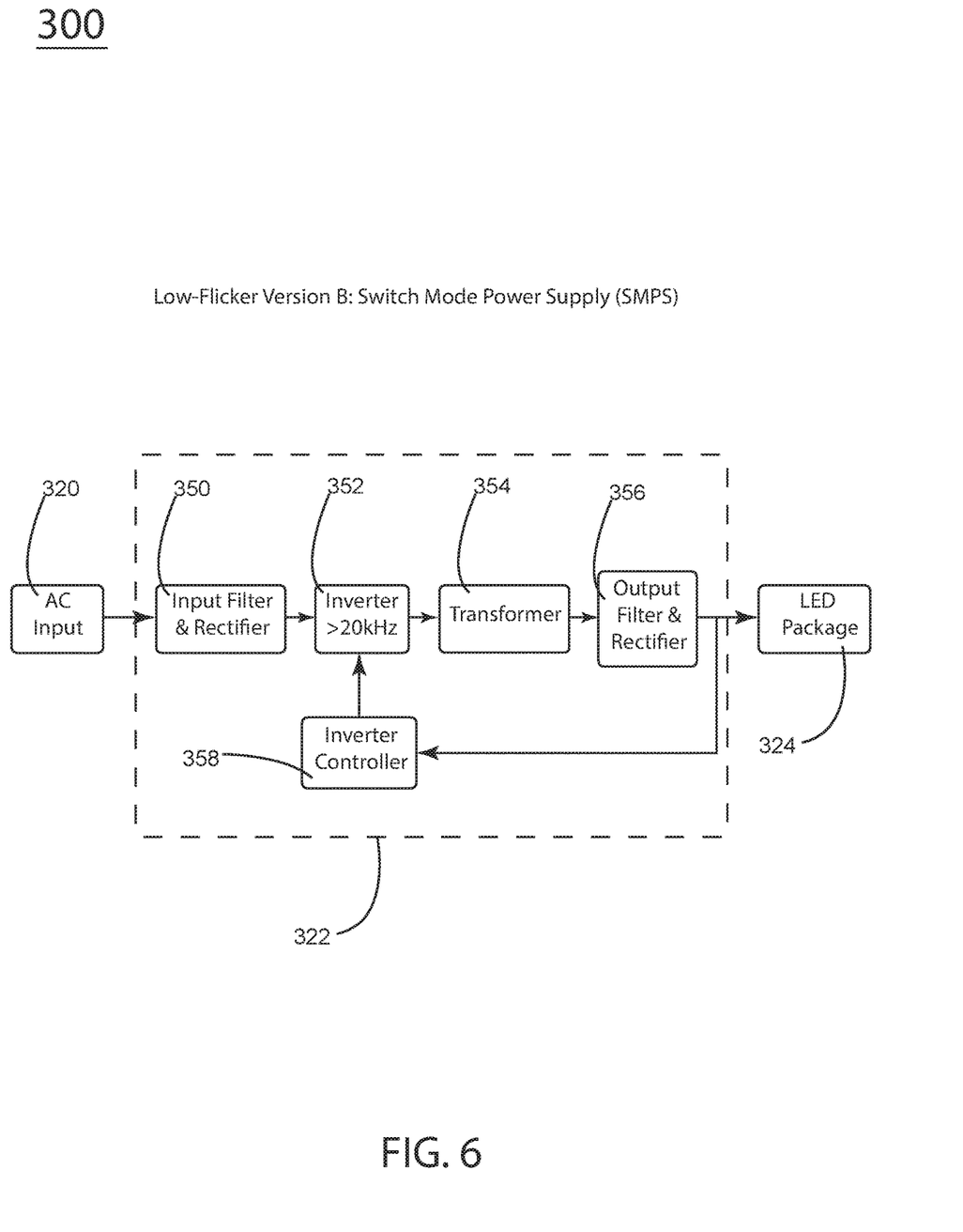
FIG. 6 is an iteration of the example electronic schematic of a low-flicker driver of the embodiment of FIG. 5.

FIG. 6 is a diagram depicting an iteration of a low-flicker driver 322 of the present embodiment, briefly described in FIG. 4. One skilled in the art may recognize this LED driver iteration as a switch-mode power supply, otherwise referred to as a switching power supply. An AC input 320 powers the low-flicker driver 322. The low-flicker driver 322 is comprised of an input filter and rectifier 350 electronically coupled with an inverter 352 operating at at least 20 kHz; and a transformer 354 and an output filter and rectifier 356 that powers an LED array (LED package) 324. The connection between the output filter and rectifier 356 and the LED array is interrupted by a connection to an inverter controller 358, which provides feedback to the inverter 352.

Figure 7:
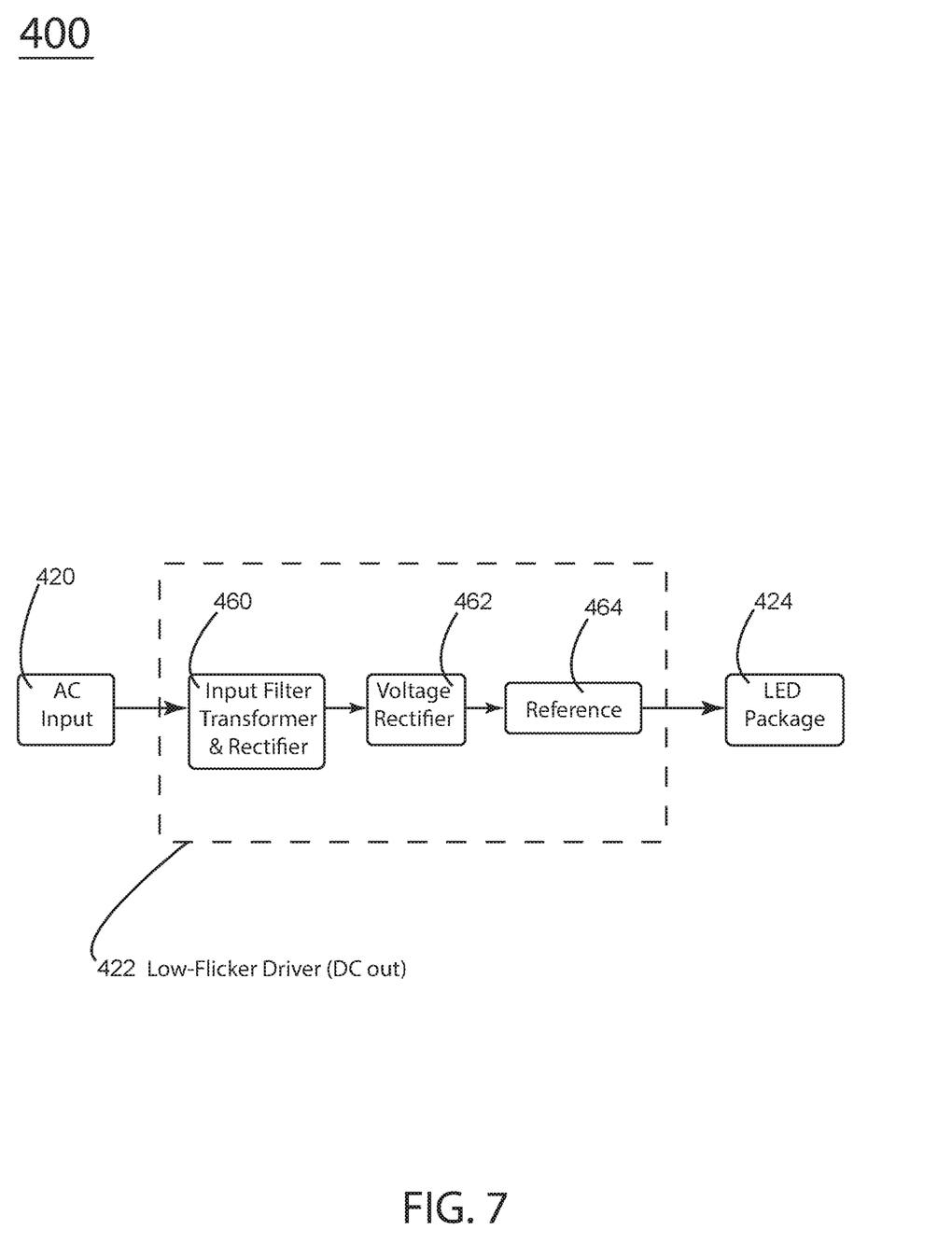
FIG. 7 is an additional iteration of the example electronic schematic of a low-flicker driver of the embodiment of FIG. 5.

FIG. 7 is a detailed diagram depicting an iteration of a low-flicker driver 422 of the present embodiment (briefly described in FIG. 4). One skilled in the art may recognize this LED driver iteration as an example of a constant current power supply. An AC input 420 powers the low-flicker driver 422. The low-flicker driver 422 is comprised of an input filter, transformer, and rectifier 460 that powers a voltage rectifier 462 that continues to a voltage reference 464 that powers an LED package 424.

Figure 8:
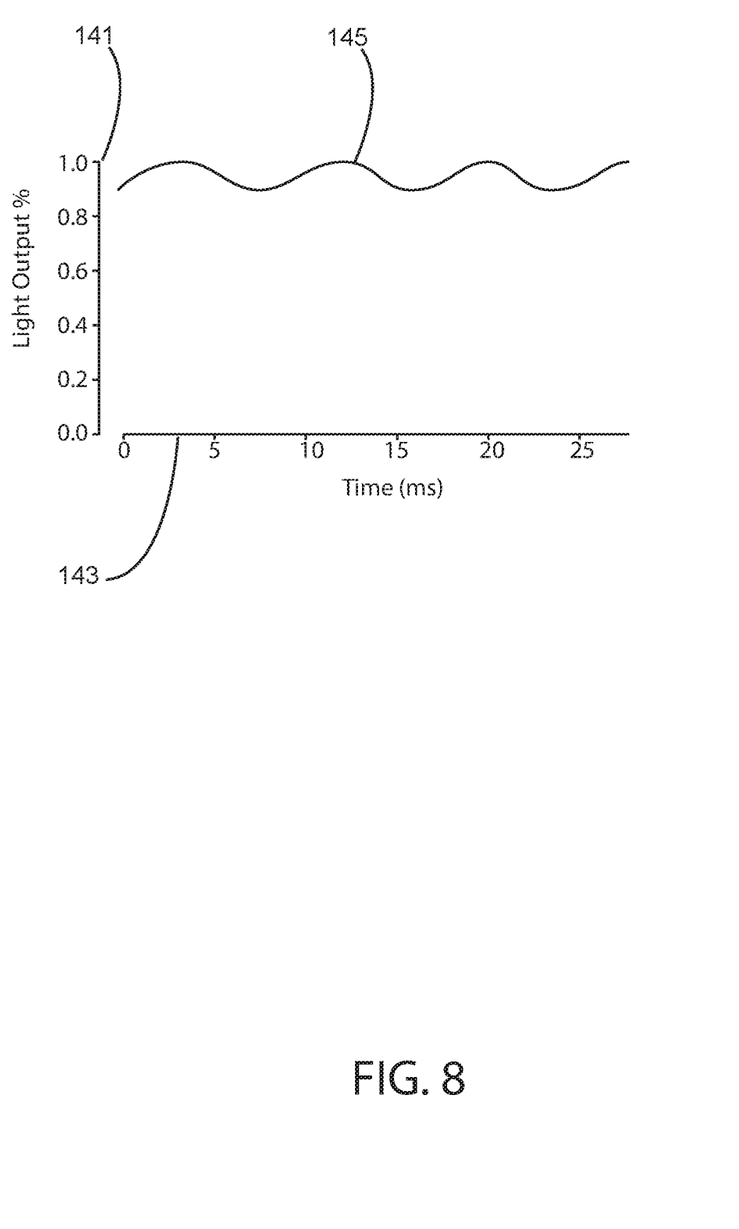
FIG. 8 is a graph depicting the percent flicker modulation of the present embodiment.

FIG. 8 is a graph depicting the range of flicker of the embodiment. Light output is represented in the vertical axis 141 and time is represented in milliseconds on the horizontal axis 143. Flicker is represented by line 145. One skilled in the art understands that the graph depicts a flicker modulation of approximately 10% at approximately 120 Hz. One skilled in the art understands that a similar design may operate at less than 10% at this frequency.

Figure 9:
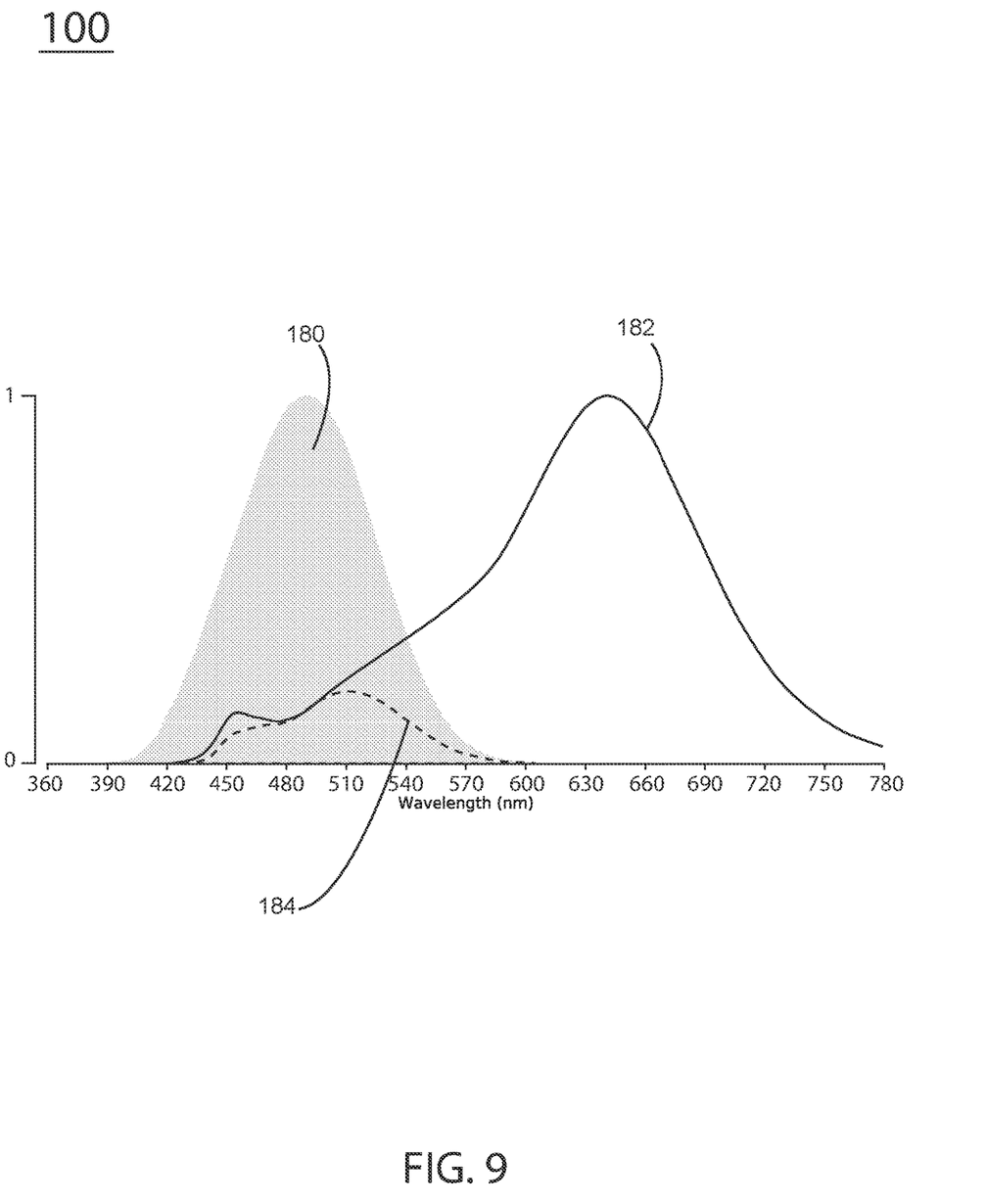
FIG. 9 is a graph depicting the spectral power distribution of the present embodiment.

FIG. 9 is a graph that depicts the characteristics of the embodiment's light. One skilled in the art recognizes this graph as a spectral power distribution (SPD). The vertical axis represents the relative intensity of each wavelength. A gray area 180 depicts the wavelengths that lie within the range of melanopic sensitivity, approximately 410-570 nm, peaking at approximately 490 nm. Within the range of melanopic sensitivity 180, is an area surrounded by dashed lines 184, depicting the range of light within the area of melanopic sensitivity 180 that is produced by the embodiment. The relative intensity of the light per wavelength produced by the embodiment is shown in the area 182, demonstrating that the light source produces some amount of light at all wavelengths spanning approximately 430 nm to 780 nm. The peak wavelength is a red color in the area of 630-650 nm. This specific SPD represents high-fidelity ~2200 Kelvin light appropriate for evening reading, with a balance of low melanopic input, with a total of 0.39 melanopic lumens. One skilled in the art understands the range of human vision is narrower than the x-axis of the graph shown.

Figure 10:
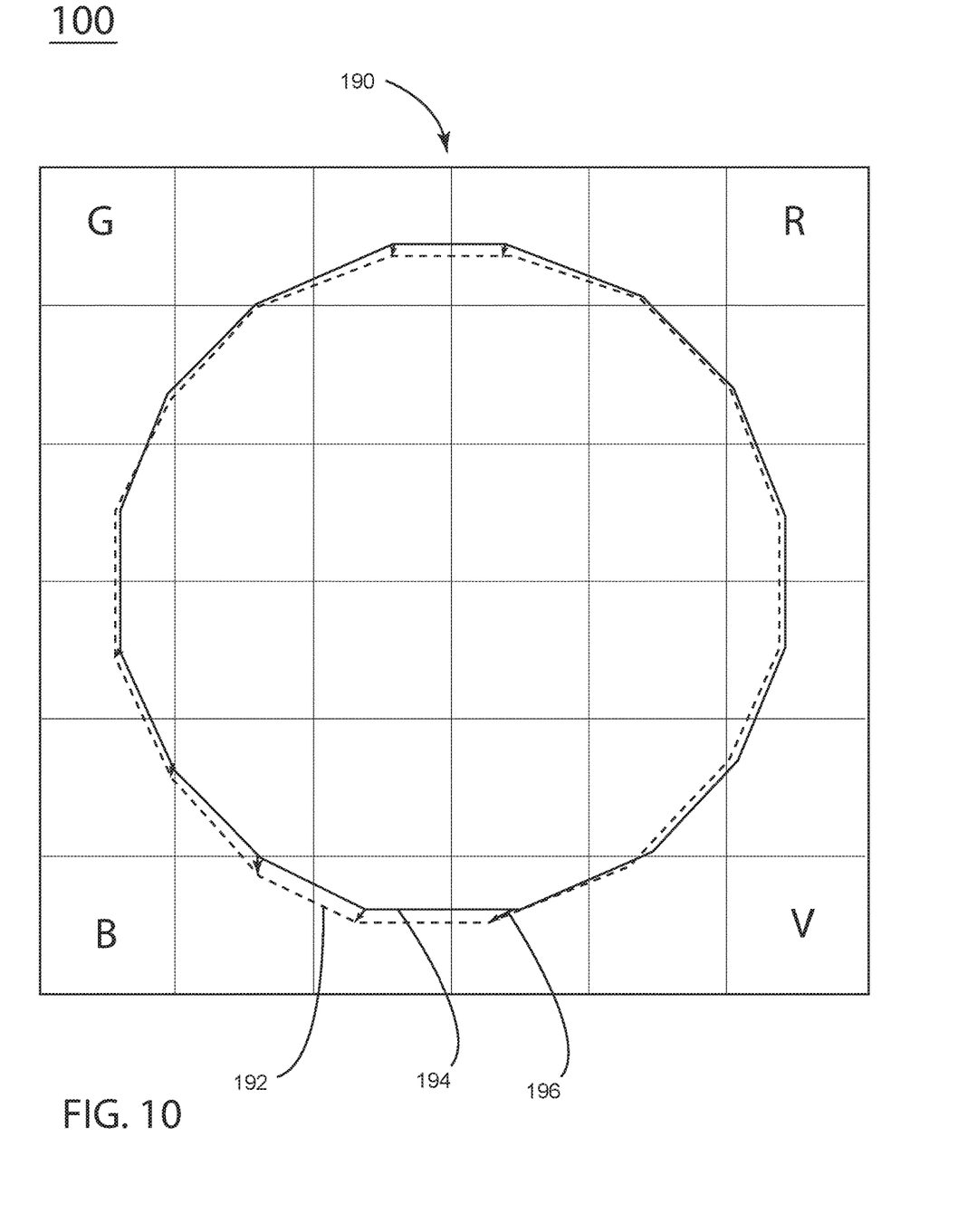
FIG. 10 is a TM-30-15/18 vector graphic depicting the hue and saturation of the embodiment.

In FIG. 10, one skilled in the art recognizes that the graph 190 is a TM-30-15/18 color vector graphic with Red (R) Blue (B) Green (G) and Violet (V) in each corner of the graph.

The graph 190 illustrates average hue and saturation over 16 hue bins. The reference or neutral light source 194 is a polygon with nodes residing on a near-perfect circle, represented by a solid line. The test source 192, in this case corresponding to the embodiment and also defined by SPD 182 (FIG. 9), is represented by a dashed line. Arrows 196 show color distortions: if the dashed test line is inside the solid reference line, the light source is relatively desaturated for that hue range. If the red line is outside the blue line, the light source is relatively oversaturated for that hue range. Tangential arrow directions indicate a shift in hue. The dashed line is neither highly oversaturated nor highly desaturated for this test source, which is why it has a neutral Rg in the range of 95-105.

These embodiments should not be construed as limiting.

The invention claimed is:

1. A light-emitting diode (LED) lamp, comprising:
an array of LED packages arranged inside a glass container; and
each of said LED packages having an upper electrical connection and a lower electrical connection for powering each LED package; and
said upper and said lower electrical connections arranged radially about the center of the array; and
said upper electrical connections rotated with respect to said lower electrical connections according to the equation:

$$R = \frac{360}{n}$$

where R=the degree of counterclockwise rotation of the upper contacts with respect to the lower electrical contacts, and n is the number of LED packages; and
power-conditioning electronics contained within a lamp base are electrically coupled with said upper and said lower electrical connections; and
said power-conditioning electronics receiving AC; and
said AC powering a low-flicker driver that converts AC to DC to power said LED array; wherein
power, conditioned by said power-conditioning electronics, is provided to the lamp, and the powered LED packages arranged in said array emit light without emitted shadows.

2. The LED lamp of claim 1 wherein the glass container is semi-opaque.

3. The LED lamp of claim 1 wherein the glass container is opaque.

4. The LED lamp of claim 1 wherein said upper electrical connections further rotated with respect to said lower electrical connections according to the equation:

$$R = \frac{360}{n+x}$$

where x is a number greater than 0 resulting in an array that is relatively farther rotated.

5. The LED lamp of claim 1 wherein said upper electrical connections further rotated with respect to said lower electrical connections according to the equation:

$$R = \frac{360}{n-x}$$

where x is a number greater than 0 resulting in an array that is relatively less rotated.

6. The LED lamp of claim 1 further comprising:
each LED package in said array being a blue LED having a peak wavelength of approximately 450 nm coated with a phosphor; and
when illuminated by said power electronics, said LED in combination with said phosphor produces light; and
said light being approximately 2200 Kelvin; and
said light having a melanopic ratio between 0.30 and 0.40; and
said light having an output of between 250 and 450 lumens; and
said light having an output of between 75 and 180 melanopic lumens; wherein
color and temperature of said light renders printed text and images appropriate for reading while providing relatively high color rendering, relatively warm correlated color temperature and relatively low melanopic input.

7. A light-emitting diode (LED) lamp, comprising:
an array of LED packages arranged inside a glass container; and
each of said LED packages having an upper electrical connection and a lower electrical connection for powering each LED package; and
said upper and said lower electrical connections arranged radially about the center of the array; and
said upper electrical connections rotated with respect to said lower electrical connections according to the equation:

$$R = \frac{360}{n}$$

where R=the degree of counterclockwise rotation of the upper contacts with respect to the lower electrical contacts, and n is the number of LED packages; and
power-conditioning electronics contained within a lamp base; and
said power-conditioning electronics receiving AC; and
said AC powering a low-flicker driver that converts AC to DC to power said LED array; and
each LED package in said array being a blue LED having a peak wavelength of approximately 450 nm coated with a phosphor; and
when illuminated by said power electronics, said LED in combination with said phosphor producing a light; and
said light being approximately 2200 Kelvin; and
said light having a melanopic ratio between 0.30 and 0.40; and
said light having an output of between 250 and 450 lumens; and
said light having an output of between 75 and 180 melanopic lumens; wherein
power, conditioned by said power-conditioning electronics, is provided to the lamp; the powered LED packages arranged in said array emit light without emitted shadows; and color and temperature of said light renders printed text and images appropriate for reading while providing relatively high color rendering, relatively warm correlated color temperature and relatively low melanopic input.

8. The LED lamp of claim 7 further comprising:
said light between 100 and 200 lx; and
said light having a minimum CRI Ra of 93; and
said light having a minimum R9 of 50; and
said light having a minimum Rf of 85; and
said light having an Rg between 97 and 103; and
said light having blue light between 440 and 490 nm; and
said light having green light between 490 and 570 nm; and
a melanopic ratio preferably 3.9.

9. The LED lamp of claim 7 further comprising:
a linear LED driver; and
the linear LED driver electronically coupled with an electrolytic capacitor between 10 uF and 20 uF; and
a full-wave bridge rectifier; wherein
resultant flicker modulations are less than 10% at frequencies between 100 Hz to 999 Hz.

10. The LED lamp of claim 7 further comprising:
a switch-mode power supply as the LED driver; and
a full-wave bridge rectifier; wherein
resultant flicker modulations are less than 30% at frequencies between 1 kHz to 9.99 kHz.

* * * * *